United States Patent [19]

Putz

[11] Patent Number: 5,285,540

[45] Date of Patent: Feb. 15, 1994

[54] TOILET TRAINING SYSTEM

[75] Inventor: Lawrence J. Putz, Grand Junction, Colo.

[73] Assignee: Samantha Bell, Little Rock, Ark.

[21] Appl. No.: 609,521

[22] Filed: Nov. 5, 1990

[51] Int. Cl.⁵ .............................................. A47K 17/00
[52] U.S. Cl. ...................................................... 4/661
[58] Field of Search ................................ 4/300.3, 661

[56] References Cited

U.S. PATENT DOCUMENTS

| D. 308,989 | 7/1990 | Cohen | D20/39 |
| 4,010,497 | 3/1977 | Menter et al. | 4/300.3 |
| 4,744,113 | 5/1988 | Kogut | 4/661 |

FOREIGN PATENT DOCUMENTS 2560763  9/1985  France .................................... 4/242

OTHER PUBLICATIONS

Little White House Enterprize May 25, 1990.

Primary Examiner—Charles E. Phillips
Attorney, Agent, or Firm—Timothy J. Martin; Dana S. Rewoldt

[57] ABSTRACT

A toilet training system and method which includes a plurality of sheets with patterns adapted to dissolve when contacted with urine, at least one chart for recording the child's use of a toilet, instruction for positioning one of the sheets in the toilet such that the patterned sheet is contacted by the child's urine and therefore dissolves, and instructions for recording the child's toilet training progress on the provided chart. Optionally receiving means are positioned in the toilet to hold the sheet out of the water and in line with the child's urine stream. The sheet is preferably formed of carboxymethyl cellulose and sized to dissolve when contacted with 30 cc of urine. In the preferred embodiment this toilet training system and associated method of encouraging child to use the toilet is in a booklet form.

10 Claims, 4 Drawing Sheets

TOILET TRAINING SYSTEM

BACKGROUND OF INVENTION

The present invention is directed to a toilet training system useful in encouraging small children to control their excretory system and eliminate urine and fecal matter in a toilet or potty. The training system includes a combination of urine dissolvable sheets, a chart for recording potty training progress, and instructions that explain how to use the sheets and chart for potty training.

Toilet training or potty training (toilet and potty shall hereinafter by considered reversible terms) has been causing new parents concern for centuries. The process of helping a child achieve control of his excretory systems so that diapers are no longer necessary can be a frustrating process for both the child and the training adult. Typically, the child is introduced to the idea of potty training by watching adults use the toilet. A child's potty or a seat adapted to fit on the adult toilet can be used to begin the actual toilet training process.

In the past, various systems for training children have been introduced. For example one system requires the child be placed on the toilet every 15 minutes for a period of 5 minutes each. When the child eliminates while on the potty they are praised. Another system parents use is watching for warning signals of bowel movements such as turning red, grunting, or straining, then placing the child on the potty to complete the activity. Few children train in a matter of days or even weeks, it usually takes months. The length of the training period often has to do with the child's interest or lack thereof in sitting on the potty. To many children the potty is uninteresting and requires time away from toys and other entertainment.

To enhance a child's interest in using the potty certain training systems encourage the adult to place floatable toys in the toilet to entertain the child. These toys are inconvenient in that they are in contact with urine and fecal matter and they must be removed prior to flushing the eliminated matter. The present invention is directed to a potty training system which employs a patterned sheet dissolvable in urine and a method of use that enhances a child's interest in becoming potty trained. The development of paper-like material capable of being dissolved in liquid was originally employed by the U.S. government for espionage activity. This type of material is also employed in certain types of welding activities.

SUMMARY OF THE INVENTION

It is an object of the present invention to provide a new and useful potty training system containing all the elements necessary for stimulating a child's interest in using the toilet for eliminating excreta.

It is another object of the present invention to provide a nontoxic, biodegradable, decorative sheet which a child can dissolve, or make disappear by urinating on the sheet.

It is also an object of the present invention to provide a new and useful potty training system, containing all the elements necessary to encourage a child's use of the toilet for elimination, in a book.

A further object of this invention is to capture a child's interest in using a potty by allowing the child to perform "magic" by making the decorative sheet in the toilet disappear.

To accomplish these objects, the adult can explain to the child prior to permitting the child to urinate in the toilet, that the patterned sheet will dissolve when contacted with urine, whereby causing the child to be interested in urinating on the patterned sheet. After urination by the child in the toilet the adult should praise the child. The final step in the toilet training exercise can include recording the child's progress in the use of the toilet for elimination of urine on the chart.

These and other objects of the present invention will become more readily appreciated and understood from a consideration of the following detailed description of the preferred embodiment when taken together with the accompanying drawings.

DETAILED DESCRIPTION OF THE PREFERRED EMBODIMENT

Figure 2:
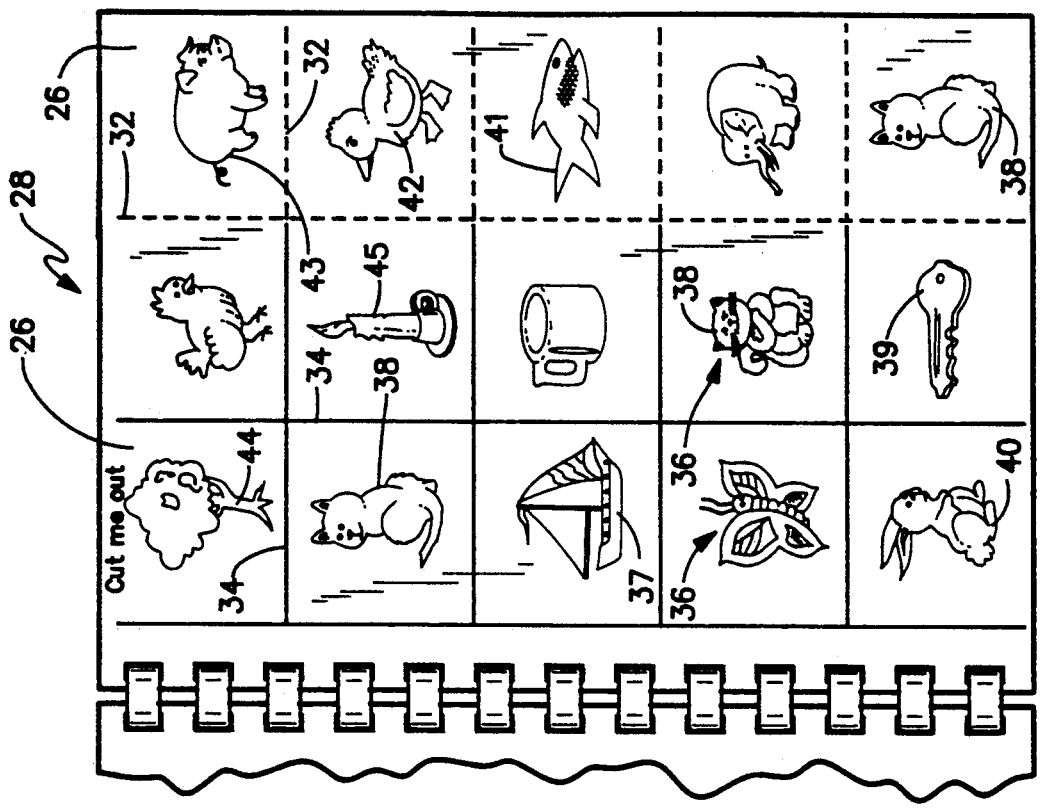
FIG. 2 is a front plan view of a page containing a plurality of sheets according to the present invention.

The present invention is directed to a toilet training system which provides all the necessary elements and correlating instruction for stimulating a child's interest in using a toilet for elimination of excreta. As such, the system according to the present invention includes the urine dissolvable sheets, charts for recording the progress made in potty training, and instructions necessary for a person to potty train a young child by employing this system.

As is shown in FIGS. 1-4 the toilet training system can be packaged as a booklet 10. The toilet training system includes at least one chart 20 for recording the child's progress in using the toilet for elimination functions, at least one sheet 26, or a page 28 containing a plurality of sheets which are divisible portions 30 of the page 28, and instructions 46. Thus booklet 10 presents a pleasing appearance and an efficient method for display and sale of the toilet training system.

Figure 1:
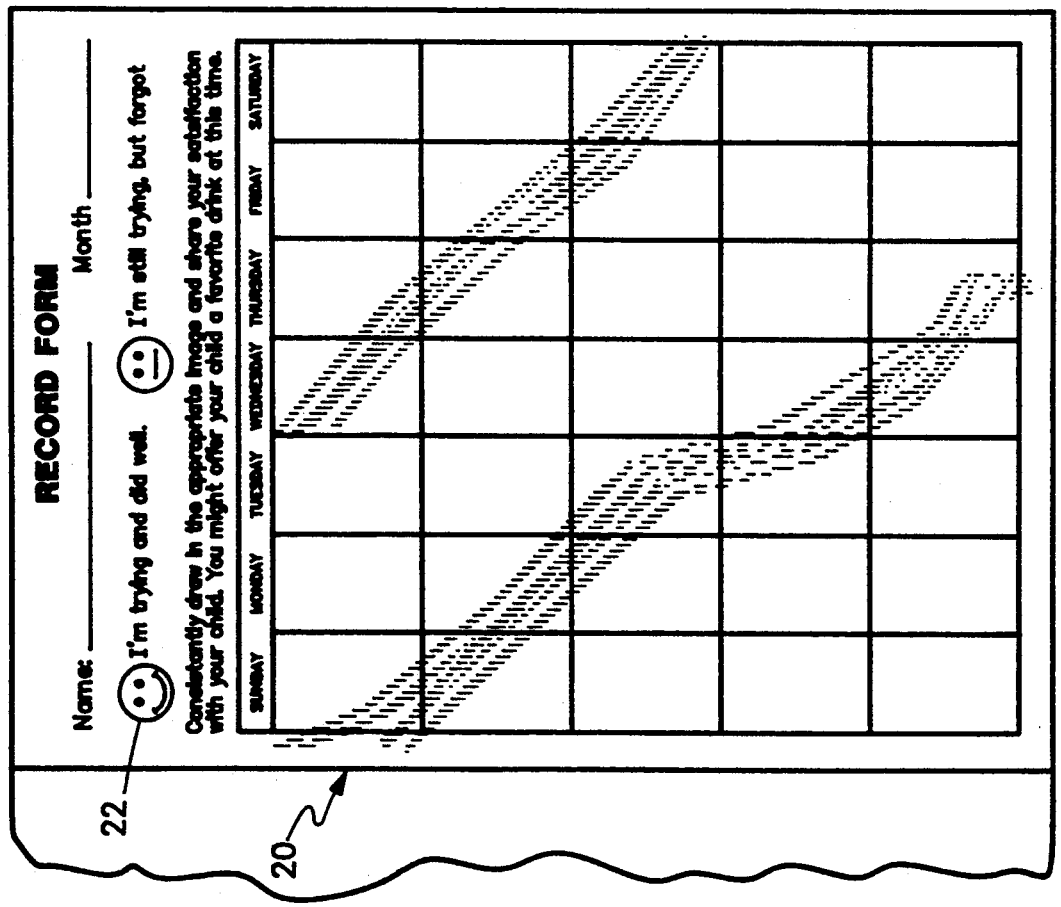
FIG. 1 is a front plan view of a recording chart according to the present invention.
Figures 3, 4:
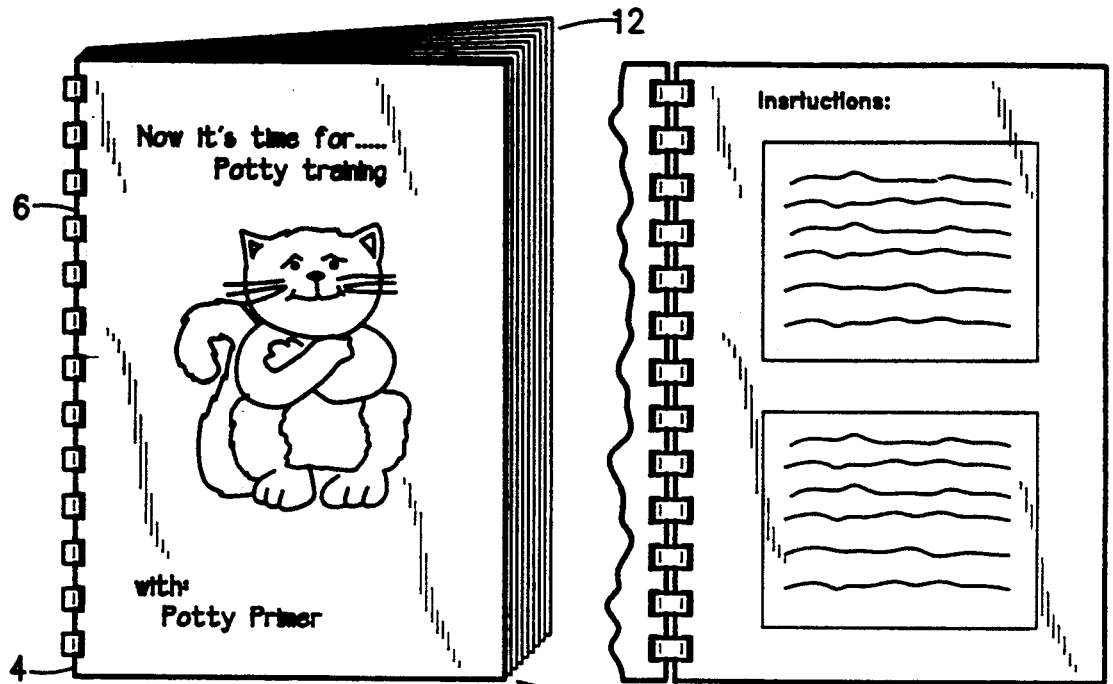
FIG. 3 is a front plan view of toilet training system formed as a booklet according to the present invention.
FIG. 4 is a front plan view of an instruction sheet according to the present invention.

With greater detail as is shown in FIG. 3, the booklet 10 includes a plurality of sheets 26 forming page 28 as shown in FIG. 2, a chart 26 shown in FIG. 1 and instructions 46 as shown in FIG. 4 that in combination form a booklet 10 having a plurality of leaves 12 bound together at location 14 to form spine 16.

Turning to each element of the toilet training system in greater detail starting with the sheets shown in FIG. 2; the sheets 26 which can form a page 28 are removably detachable one from another. The page 28 can have perforation 32 between each sheet 26 or cutting lines 34 between each sheet 26 to make detachment of the sheet easier. The sheet 26 appears paper-like and is capable of being printed on by letterpress and dryoffset using water soluble or oil based inks. In the preferred embodiment of the present invention each sheet 26 has a decorative design 36 imprinted thereon. These decorative designs 36 can be formed of water soluble ink or oil based ink but preferably an oil based ink is employed.

Alternatively the sheets 26 can be formed in shapes that interest children and/or in colors that interest children. Examples of decorative designs 36 include boats 37, cats 38, keys 39, rabbits 40, fish 41, ducks 42, pigs 43, trees 44, candles 45 and the like. It has been determined that the more ink used in the sheet 26 to form the design 36 the less useful the sheet 26 becomes as a potty training tool. The sheet 26 specifically adapted to dissolve when contacted with urine. Preferably the sheet 26 is formed of 50% carboxymethyl cellulose and wood pulp, and more preferably the sheet 26 is formed of 80% carboxymethyl cellulose and 20% wood pulp. The sheet 26 is specifically formed of a material of a type and size to dissolve when contacted with urine in the amount produced by a small child. It has been determined that the average small child will produce approximately 30 cc of urine. Thus when the preferred material is employed the sheet 26 should be approximately a 2"×2" square. This size permits the amount of urine eliminated by a child to disperse or dissolve the sheet in less than two minutes. Thus the child does not lose interest in the patterned sheet 26 prior to its disappearance. If a large amount of ink is employed to make a pattern, the amount of liquid and the amount of time necessary for disperssment of the sheet 26 into the urine increases. Thus if the pattern is totally colored, a proportionately smaller sheet should be employed to produce disappearance by the sheet in the urine in a set amount of time.

Turning to FIG. 1 an element in the toilet training system is shown in detail. The chart 20 can be used to record the child's progress in eliminating in the toilet bowl. This chart 20 is adapted to offer the child incentive to earn a smiley face 22 for the day. Keeping a written chart 20 of the progress potty training is beneficial for both the child and the adult. Other charts can be provided in the toilet training system to enhance and speed up the child's toilet training. These charts can include the time of day the child usually urinates, the signs and signals the child gives prior to elimination, the number of times a day the child eliminates and where the elimination takes place. By recording a child's elimination habits the adult can often place the child on the potty prior to having an accident happened to the child.

FIG. 4 depicts the instruction pages 46. The instructions 46 are for using the chart 20 and the sheet 26 in the toilet training system. The instructions 46 generally include first instructions detaching a sheet 26 from one of the pages 28, and for positioning one of the plurality of sheets 26 in the toilet, see FIG. 5, such that the child's elimination of urine in the toilet causes the sheet 26 to dissolve. The instructions 46 also give the trainer directions to explain to the child that elimination of urine in the toilet will make the sheet 26 dissolve and disappear. To capture the child's interest the adult can tell the child that this is the child's magic that causes the patterned sheet 26 to disappear.

Figure 5:
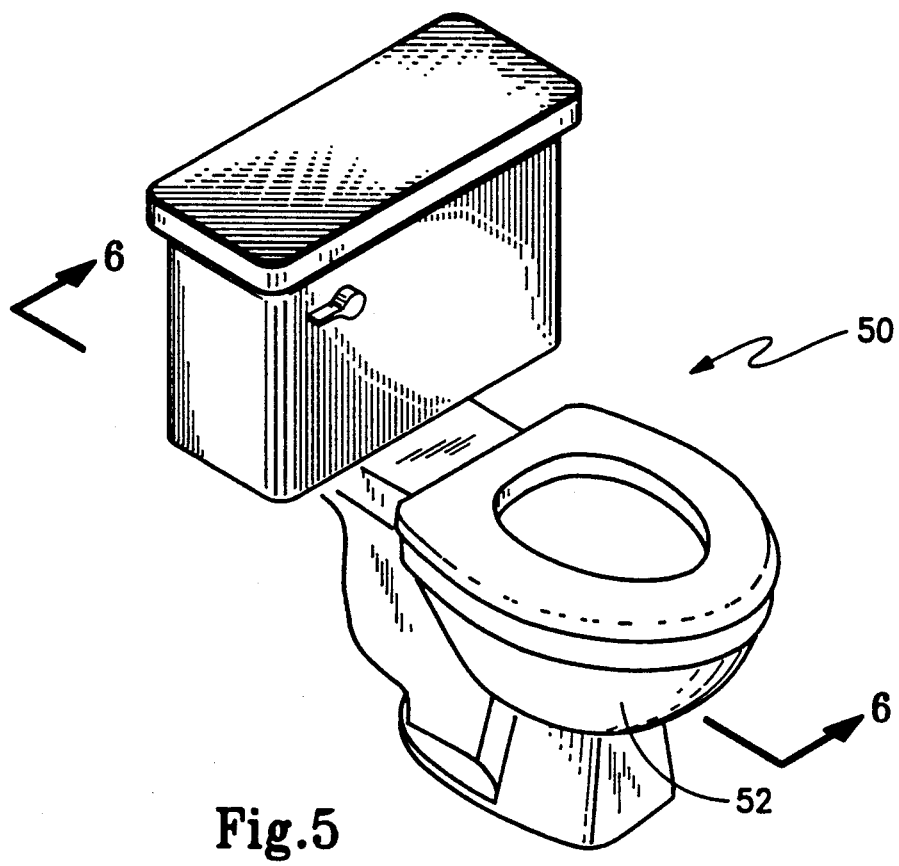
FIG. 5 is a side perspective view of a toilet.
Figure 10:
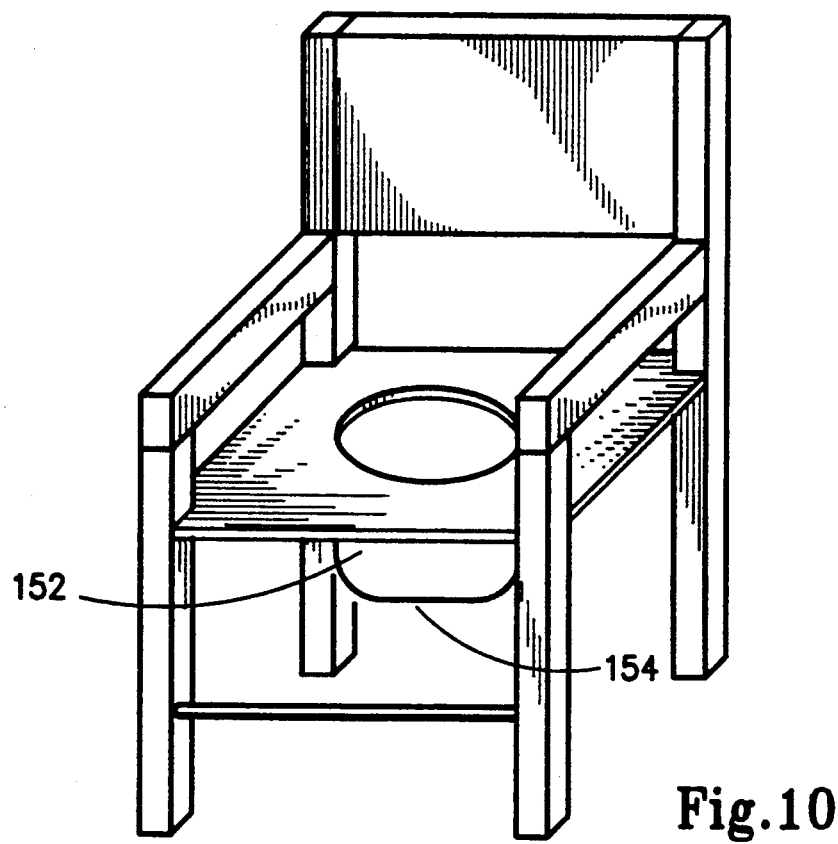
FIG. 10 is a front view of a child's potty chair.

Further, the first set of instructions 47 explain that the sheet 26 should be positioned and placed on a dry surface in the toilet bowl 52. Turning to FIGS. 5 and 10 it is obvious that if the child is training in a child's potty chair 80 as shown in FIG. 10 the potty bowl 152 has a dry surface 154 until the child eliminated in the bowl 152. Thus the sheet 26 can be placed on the bottom surface 154 of the bowl 152 of a potty chair 150 which is employed for training. Likewise a potty training device having a bowl 152 with a dry bottom surface 154 adapted to be placed on the toilet 50 as shown in FIG. 5, can easily be employed.

Figure 6:
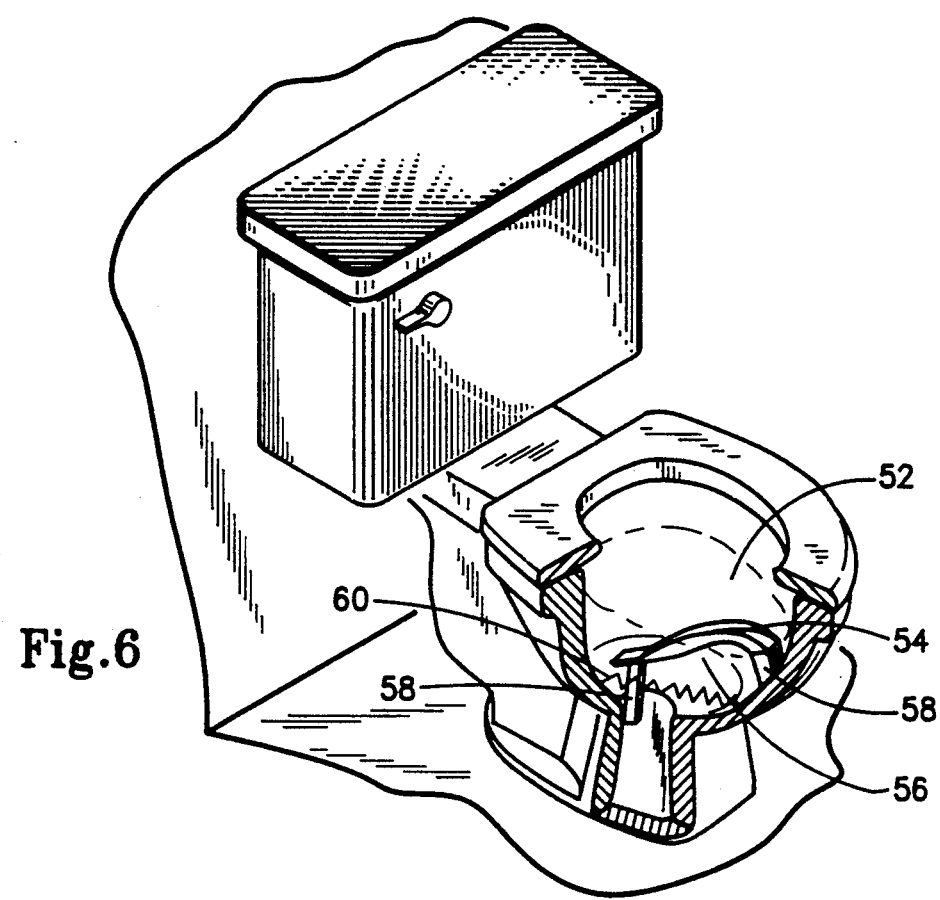
FIG. 6 is a cross-section about lines 6—6 of FIG. 5 including receiving means according to the present invention.

However, if the child is being trained on a toilet 50 as shown in FIG. 5 receiving means 56 adapted to maintain the sheet 26 in a dry area within the toilet bowl 52 may be employed. These receiving means 56 must be capable of placing the sheet 26 in a position to be contacted by the child's urine. The receiving means 56 can generally take a variety of forms including flotation device. Examples are shown in FIGS. 6 and 10. FIG. 10 shows the simplest form, the bottom surfaces 54 of a bowl 52. The receiving means 56 in whichever embodiment includes a dry surface 54 positioned to be contacted with urine and positioning means 58 which are adapted to maintain the receiving means 56 in a set location relative to where the child is seated. Turning to FIG. 6 which is a cross-section of FIG. 5 about lines 6—6 it reveals the receiving means 56 which has a dry surface 54 which is above the water level 60 and positioning means 58 adapted to maintain the receiving means 56 in a position to be contacted by the child's urine.

Figure 7:
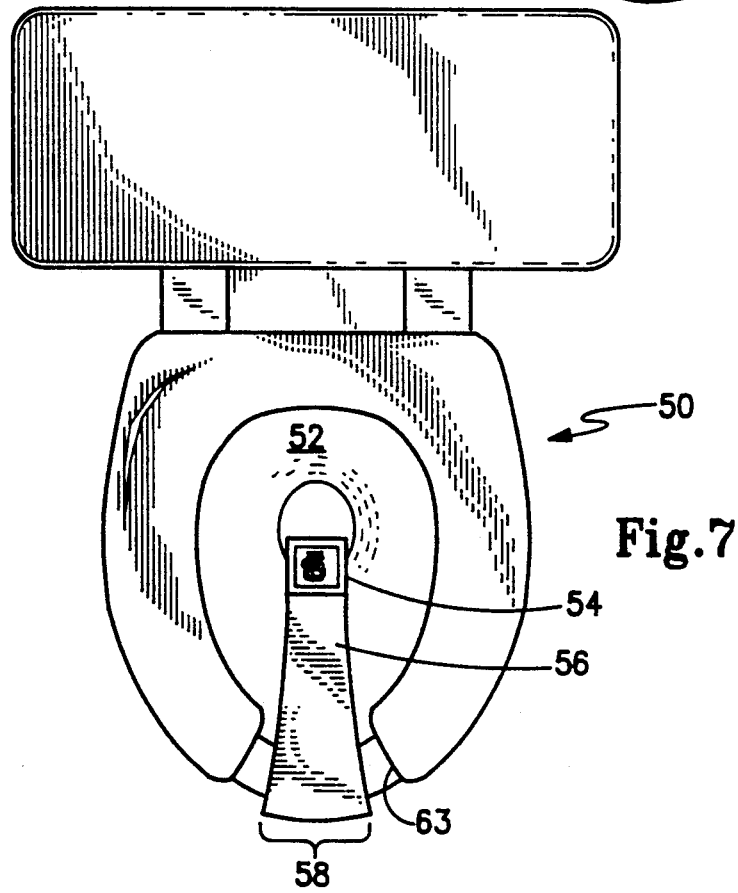
FIG. 7 is a top perspective view of an alternative embodiment of the receiving means.
Figure 8:
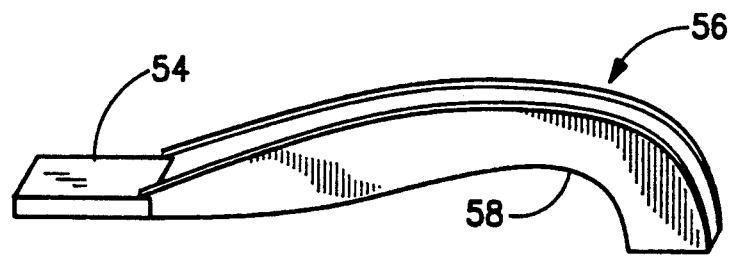
FIG. 8 is a perspective side view of the receiving means shown in FIG. 7.

FIG. 7 and 8 show two views of the same receiving means 56 which has positioning means 58 adapted to connect the receiving means 56 to the rim 63 of the bowl 52, such that the dry surface 54 is positioned to be contacted with a child's urine.

Figure 9:
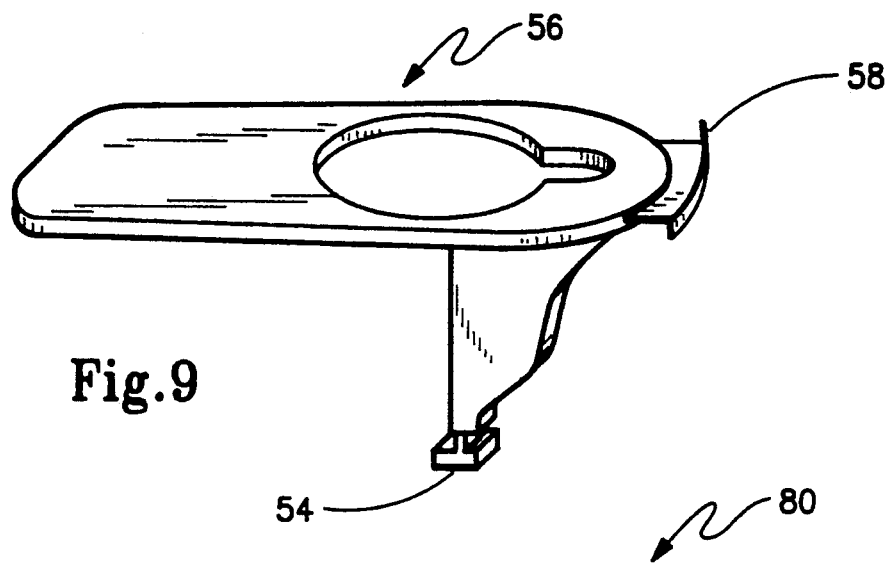
FIG. 9 is another alternative embodiment of the receiving means.

FIG. 9 shows another alternative embodiment for the receiving means 56 which has positioning means 58 adapted to connect the receiving means 56 with the rim 63 of the bowl 52 such that the dry surface 54 is positioned to be contacted with a child's excreta. The examples of receiving means 56 shown in the drawings are not listed by way of limitation but merely as examples of any of a variety of forms the receiving means 56 could take.

The method of using this toilet training system which includes the urine dissolvable sheets 26, instructions 46, at least one progress chart 20, and optional receiving means 56 to encourage a small child to use the toilet 50 for urination include the following steps; the first time a child is being potty trained, the adult should include this primary step of introducing the child to the toilet and explaining its functions so the child has no fear of the toilet 50 or of being flushed down the toilet. This step should not be necessary after the child has begun to be trained on this toilet training system. Next the child should be allowed to select a patterned urine dissolvable sheet. The next step is placing the sheet in a dry location in the toilet, alternative receiving means 56 should be employed if necessary. Then if it is the child's first potty training attempt the adult should explain that the patterned sheet will dissolve when it is contacted with urine. Next, the child should be permitted to urinate in the toilet and the adult and child should both view the disappearance of the patterned sheet in the toilet.

The child should be praised for dissolving the sheet and using the potty. The final step includes recording the child's toilet training progress on the chart. The process should be repeated approximately every two hours or when the child indicates they whish to use the toilet.

Accordingly, the present invention has been described with some degree of particularity directed to the preferred embodiment of the present invention. It should be appreciated, through, that the present invention is defined by the following claims construed in light of the prior art so that modifications or changes may be made to the preferred embodiment of the present invention without departing from the invention concepts contained herein.

I claim:

1. A toilet training system adapted to interest a child in using a toilet for elimination of urine and recording the child's toilet training progress comprising in combination:
    a plurality of sheets adapted to dissolve when contacted with urine;
    a chart for recording a child's use of a toilet for elimination; and
    instructions including first instructions for positioning one of the plurality of sheets in the toilet such that the child's elimination of urine in said toilet causes the sheet to dissolve, second instructions for recording the child's elimination of urine in the toilet bowl on the chart; whereby when the instructions are followed the child becomes interested in using toilet for elimination because the child causes the sheet to disappear by elimination of urine in the toilet.

2. A toilet training system according to claim 1 wherein said plurality of sheets include decorative designs of a nature which would interest children.

3. A toilet training system according to claim 2 wherein said plurality of sheets are divisible portions of a single page.

4. A toilet training system according to claim 2 wherein the first instructions include detaching a sheet for positioning in the toilet from one of a plurality of pages.

5. A toilet training system according to claim 2 wherein said decorative design is formed of water soluble ink.

6. A toilet training system according to claim 2 wherein said decorative design is formed of oil based ink.

7. A toilet training system according to claim 1 wherein said first instructions includes directions to explain to said child that elimination of urine in the toilet will make the sheet dissolve.

8. A toilet training system according to claim 1 wherein the first instruction direct the positioning of said sheet to be placed on a dry surface in the toilet bowl.

9. A toilet training system according to claim 1 wherein said chart includes a section for recording the time at which the child eliminated urine in the toilet.

10. A toilet training system according to claim 1 wherein said plurality of sheets and, said chart and said instructions form a book having a plurality of leaves bound together along a spine.

* * * * *